United States Patent
Almogy et al.

(10) Patent No.: US 7,355,689 B2
(45) Date of Patent: Apr. 8, 2008

(54) AUTOMATIC OPTICAL INSPECTION USING MULTIPLE OBJECTIVES

(75) Inventors: Gilad Almogy, Kiriat Ono (IL); Bryan C. Bolt, Beaverton, OR (US); Oded Arnon, Givataiym (IL); Boaz Kenan, Portland, OR (US); Ehud Tirosh, Mevaseret Zion (IL); Michael Corliss, Beaverton, OR (US)

(73) Assignee: Applied Materials, Inc., Santa Clara, CA (US)

( * ) Notice: Subject to any disclaimer, the term of this patent is extended or adjusted under 35 U.S.C. 154(b) by 299 days.

(21) Appl. No.: 11/047,435

(22) Filed: Jan. 31, 2005

(65) Prior Publication Data

US 2006/0170910 A1    Aug. 3, 2006

(51) Int. Cl.
*G01N 21/00* (2006.01)
(52) U.S. Cl. .............. 356/237.1; 356/237.2; 356/398; 250/208.1; 250/310

(58) Field of Classification Search ..... 356/237–237.2, 356/398; 250/234, 310, 208.1
See application file for complete search history.

(56) References Cited

U.S. PATENT DOCUMENTS

| | | | |
|---|---|---|---|
| 6,621,566 B1* | 9/2003 | Aldrich et al. | ........... 356/237.1 |
| 7,109,464 B2* | 9/2006 | Cartlidge et al. | ........ 250/208.1 |
| 7,122,786 B2* | 10/2006 | Tochio et al. | ................ 250/234 |
| 2004/0159773 A1* | 8/2004 | Fein et al. | ................ 250/208.1 |
| 2004/0246479 A1* | 12/2004 | Cartlidge et al. | ........... 356/335 |

* cited by examiner

*Primary Examiner*—Layla G. Lauchman
*Assistant Examiner*—Iyabo S Alli
(74) *Attorney, Agent, or Firm*—Patterson & Sheridan LLP

(57) ABSTRACT

Apparatus and techniques for automated optical inspection (AOI) utilizing image scanning modules with multiple objectives for each camera are provided. A scanning mechanism includes optical components to sequentially steer optical signals from each of the multiple objectives to the corresponding camera.

28 Claims, 13 Drawing Sheets

DETECTION OF ARTICLE TRAVEL

MODULE 1
ILLUMINATION
PATH

MODULE 1
COLLECTION
PATH

AUTOMATIC OPTICAL INSPECTION USING MULTIPLE OBJECTIVES

BACKGROUND OF THE INVENTION

1. Field of the Invention

Embodiments of the present invention generally relate to techniques for inspecting objects and, more particularly, to an automated optical inspection technique and system utilizing multiple objectives per camera.

2. Description of the Related Art

Automated optical inspection (AOI) systems are used to inspect a wide variety of objects, such as semiconductor wafers and printed circuit boards (PCBs), for defects. Such systems typically utilize one or more image acquisition or "microscope" modules to capture images that cover the entire surface area of the object that is to be inspected. These images are then fed to some type of computer system for processing using various types of algorithms design to identify defects in the object.

Typically, each image scanning module includes an illumination source to illuminate the portion of the article under inspection, some type of front lens assembly (referred to as an objective) that guides light back to an image capture device, such as a charge-coupled device (CCD) camera. One common type of AOI system utilizes a scanning approach, whereby the inspected article is divided into (e.g., horizontal) strips and a single image scanning module is moved back and forth, collecting images for successive strips on each pass. This approach may work well in some applications, for example, where the total surface area being inspected is relatively small and the total processing throughput requirements are relatively low. However, for applications requiring higher throughput, such as web inspection, which may have relatively large surface areas to inspect (e.g., with horizontal dimensions of several feet), a scanning approach may take too much time.

These higher throughput applications typically require multiple image scanning modules, with a camera and objective per module, allowing multiple images to be processed in parallel leading to increased throughput. In general, the number of image scanning modules utilized depends on various system requirements, as well as the individual image scanning module specifications. For example, the number of image scanning modules required is generally proportional to the total surface area to inspect and the required throughput of the system, and inversely proportional to the field of view (FOV) of each objective and pixel rate of the camera. Unfortunately, high resolution cameras with high pixel rates tend to be expensive, often costing many times more than the objectives. As a result, while systems utilizing multiple image scanning modules may achieve higher throughput than systems that scan with a single module, the cost of multiple high resolutions cameras may render such systems cost prohibitive.

Accordingly, a need exists for a system and technique for automated optical inspection resulting in high throughput relative to conventional scanning systems and low cost relative to systems that utilize a single objective per camera.

SUMMARY OF THE INVENTION

The present invention generally provides systems and methods for automated optical inspection utilizing multiple objectives per camera.

One embodiment provides an automated optical inspection system. The system generally includes at least one camera and at least one image scanning module. The image scanning module generally includes, a plurality of objective modules arranged to each have a field of view covering a portion of the article during inspection and an image selection mirror mechanism movable to sequentially transfer images from the field of view (FOV) from each objective module to the camera.

Another embodiment provides an automated optical inspection system for inspecting article. The system generally includes at least one camera and at least one image scanning module. The image scanning module generally includes a plurality of objective modules with fields of view covering a portion of the article during inspection and an image selection mirror mechanism movable to sequentially transfer images from the fields of view to the camera. For some embodiments, the objective modules in each image scanning module may be arranged in a circle or an arc, allowing a distance between the objective modules and an illumination source to be substantially constant. Arranging the modules in an arc may also allow a single mirror mechanism to be used for each objective module. The image scanning modules may be positioned relative to each other so that the FOVs of the objective modules cover the entire inspected article width with at least some partial overlap.

Another embodiment provides a method for optically inspecting an article with at least one image scanning module. The image scanning module generally includes a camera, scanning mechanism, illumination source, and multiple objective modules. The method generally includes sequentially transferring images of portions of the article within fields of view (FOVs) of the multiple objective modules to the camera. The scanning mechanism may be manipulated to sequentially direct light from the illumination source to the individual objective modules and images from the individual objective modules to the corresponding camera shared by the objective modules. The images captured with the shared camera may be processed to detect defects in the article.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

The present invention generally provides apparatus and techniques for automated optical inspection (AOI) utilizing image scanning modules with multiple objectives for each camera. A scanning mechanism includes optical components to sequentially steer optical signals from each of the multiple objectives to the corresponding camera. By freezing individual field of view images, motion accuracy requirements of the translation system used to move the inspected article may be greatly reduced when compared to scanning systems, such as "flying spot" laser scanning systems or systems based on constant illumination and linear imaging devices, for example, charge coupled devices (CCDs) or time delay and integrate (TDI) CCDs that require accurate motion control.

An Exemplary Inspection System

Figure 1:
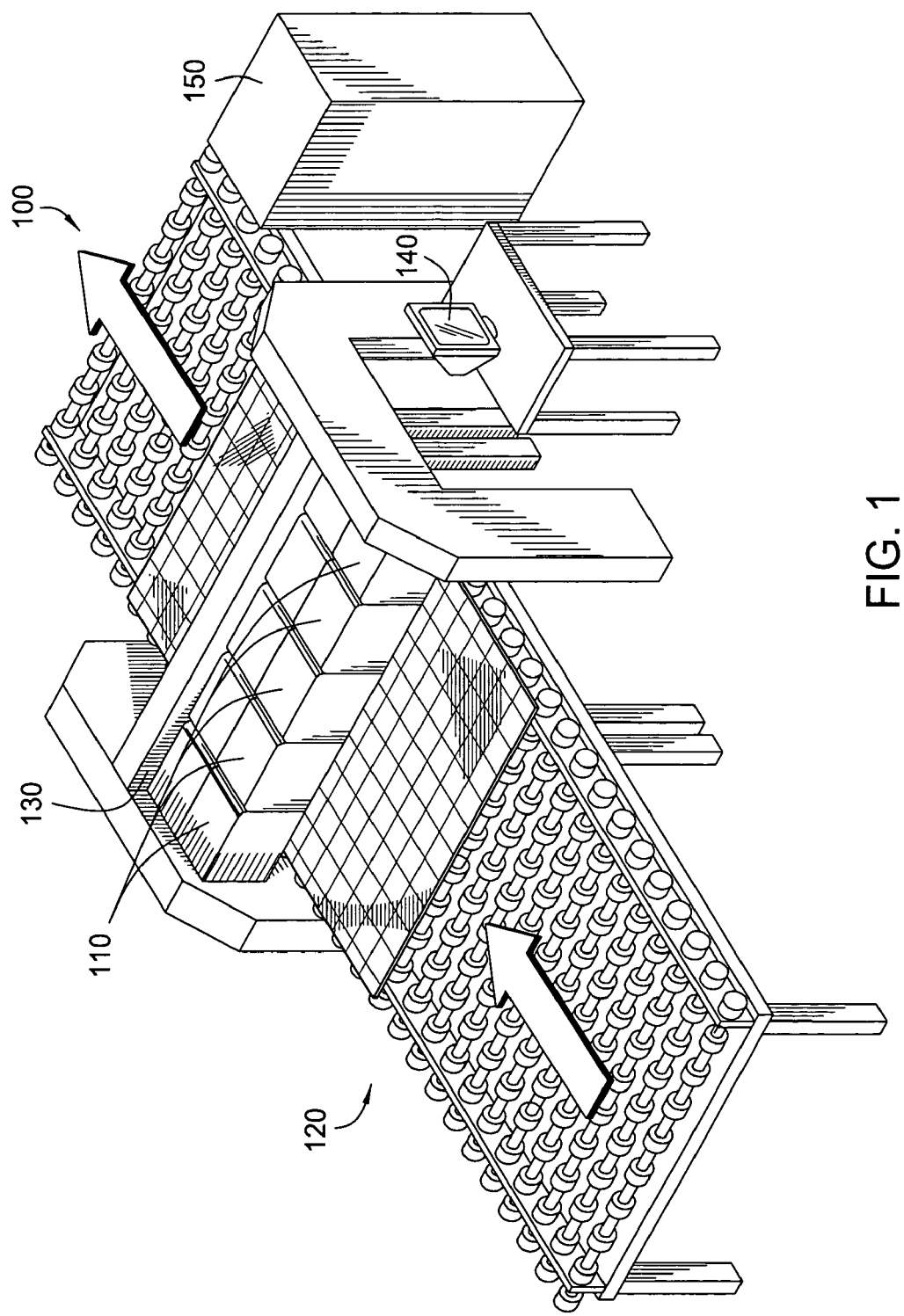
FIG. 1 illustrates an exemplary automated optical inspection (AOI) system in accordance with embodiments of the present invention.

FIG. 1 illustrates an exemplary automated optical inspection (AOI) system 100 in accordance with embodiments of the present invention. The system 100 utilizes a plurality of image scanning modules 110 to inspect the surface of an inspected article 130 for defects. As illustrated, the inspected article 130 travels under the image scanning modules 110 on a conveyer system 120. Various other types of mechanisms may also be used to move the inspected article 130 relative to the image scanning modules 110, such as a movable translation stage. For some embodiments, the inspected article 130 may be stationary while the image scanning modules 110 are moved.

Various control functions of the system 100, such as control of the conveyer 120, may be performed by a controller 150. The controller 150 may include any suitable computing and interface equipment, such as computers or programmable logic controllers (PLCs) with video capture cards to perform the control steps described herein. In some cases, an operator may control various aspects of the system 100 (e.g., conveyer speed, detection parameters, and the like) via a user interface, such as a touch screen 140 (or a conventional keyboard/mouse and display) coupled with the controller 150. In some cases, the controller 150 may display inspection results/reports or one or more images for manual inspection (e.g., by the operator) on the screen 140.

The controller 150 may also control the image scanning modules 110 to synchronize the capture of images with the movement of the article 130 under the image scanning modules 110. In general, the collective fields of view (FOVS) of the image scanning modules 110 should cover the entire article with acquired images. To account for possible inaccurate motion of the article 130 and finite accuracy of relative position of objectives modules used in the image scanning modules 110, the objective modules and image scanning modules 110 may be arranged to ensure at least some partial overlap between each.

For some embodiments, the system 100 may include a sensor (not shown) or some other means, such as detectable markings, to detect the location of the article 130 relative to the image scanning modules 110 to allow coarse synchronization between the mirror position and image acquisition commands to the article location. Increasing the accuracy of synchronization of image acquisition with conveyor movement may reduce the amount of overlap between modules and increase the system efficiency.

Figure 2A:
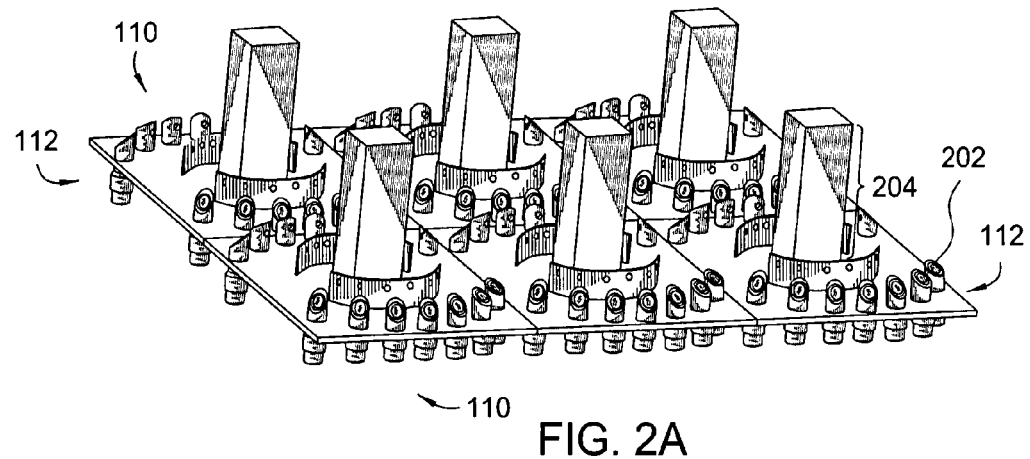
FIGS. 2A-2D illustrate various features of an exemplary image scanning module in accordance with one embodiment of the present invention.

FIG. 2A illustrates an exemplary arrangement of image scanning modules 110. As illustrated, each image scanning module 110 may include two arcs 112 of objectives modules 202 located around an optical head assembly 204 (including a camera 206). For some embodiments, each image scanning module 110 may utilize multiple optical head assemblies 204. For example, separate optical head assemblies 204 may be provided for each arc 112, in an effort to increase image capture throughput.

Figure 2B:
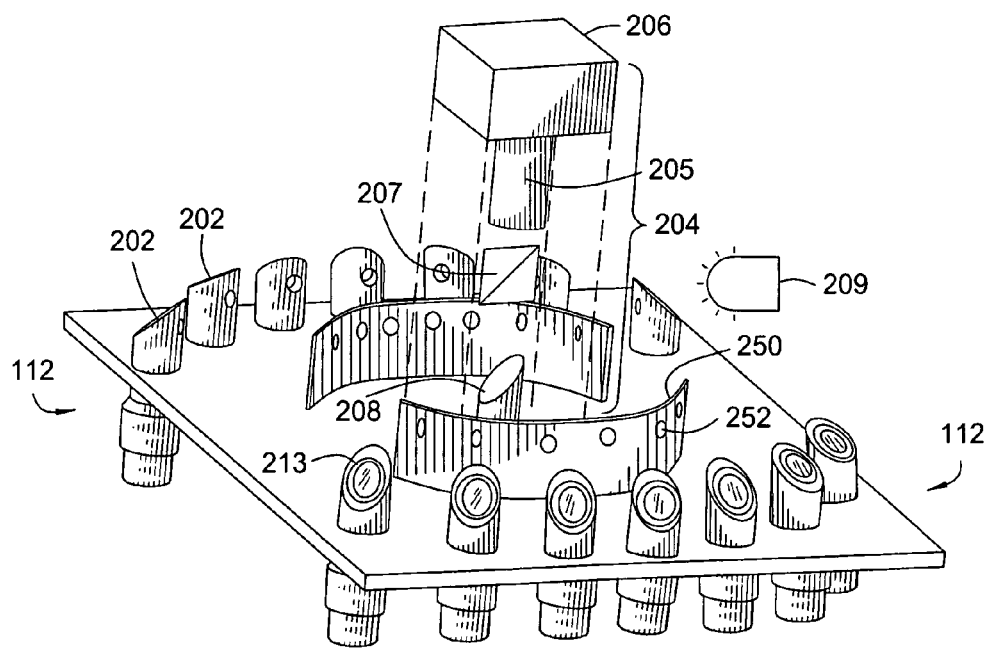

As illustrated in FIG. 2B, which shows a single image scanning module 110 in greater detail, the optical head assembly 204 generally includes a camera 206, tube lens 205, beam splitter 207, and illumination source 209. The optical head assembly 204 may also include an image selection mirror 208 used to sequentially illuminate and transfer images from each objective module 202 to the camera 206, as the inspected article 130 travels beneath the image scanning module 110. For some embodiments, some type of optical relay system may be utilized in the optical path, for example, to relay an image of the inspected article from the image selection mirror 208 to the camera 206.

Figure 2C:
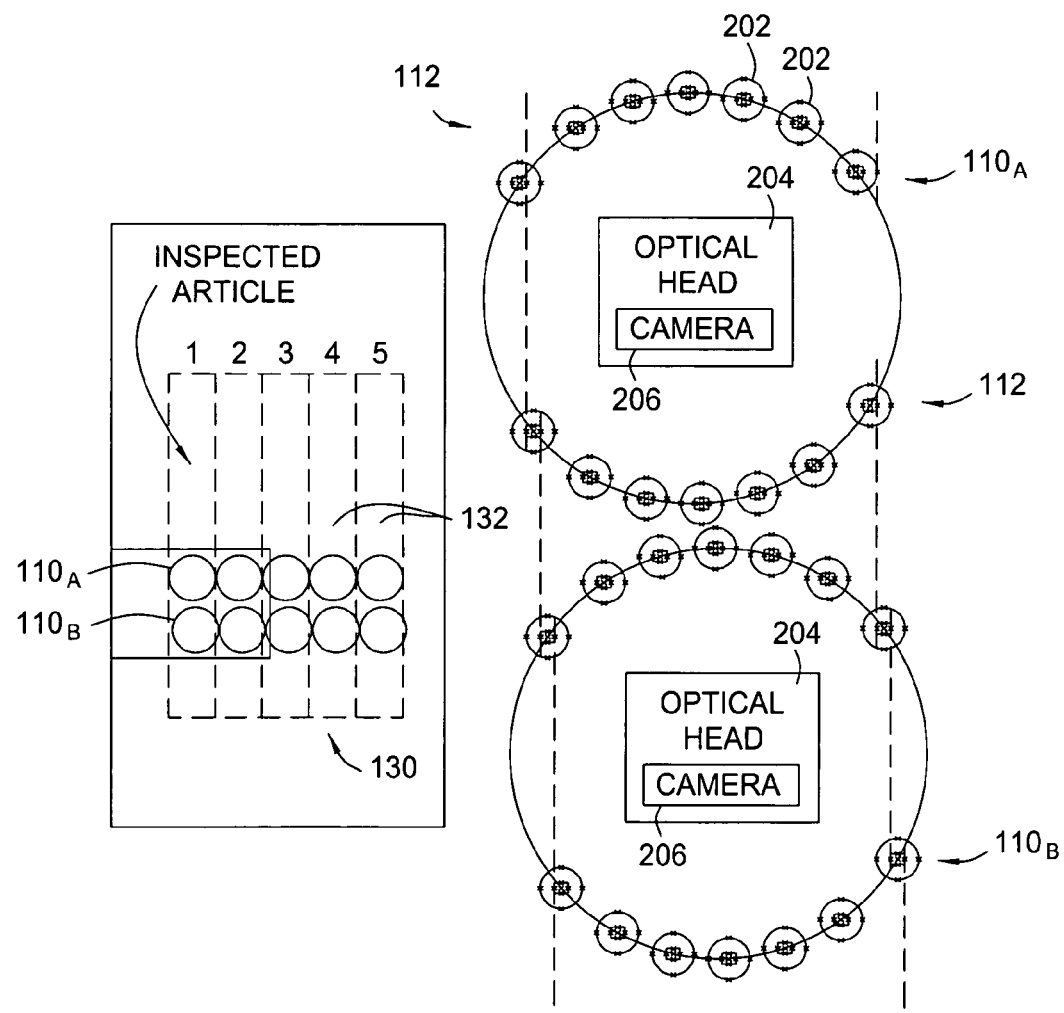

As illustrated in the top view of FIG. 2C, for some embodiments, the inspected article 130 may be divided into adjacent (e.g., vertical) regions 132, with a pair of image scanning modules 110A and 110B used to capture image portions of a corresponding region 132 as the inspected article 130 travels beneath. In other words, each such pair of image scanning modules may cover a different region 132. The image selection mirror 208 may be rotated to sequentially capture a different FOV image portion of a region 132 from each objective module 202.

Figure 2D:
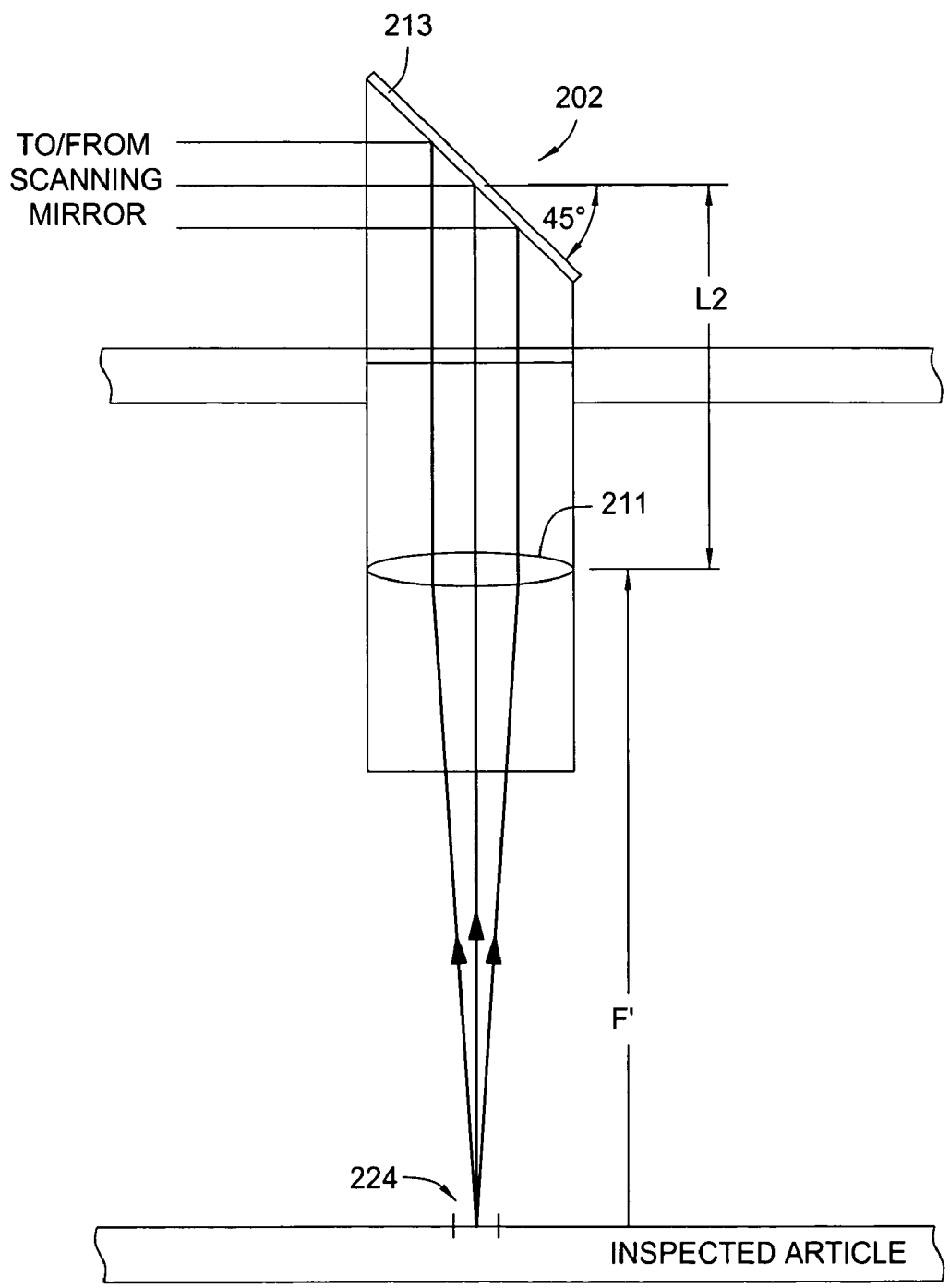

As illustrated in FIG. 2D, which shows a side view of a single objective module 202, each objective module 202 may include an objective (front end) lens 211 and a mirror 213 designed to divert the optical path from the objective lens 211 to the image selection mirror 208. For some embodiments, "periscopic scanning" may be utilized (as shown in FIGS. 3A-3D described below). For example, the optical path may be folded preferably 90 degrees by a folding mirror which is positioned at preferably 45 degrees to the optical path beyond the objective. The image selection mirror plan may also be oriented preferably 45 degrees to the optical axis and preferably 45 degrees to its rotation axis, thereby directing the optical axis back up, parallel to the rotation axis. This configuration may prevent rotation of the FOV on it's way from the inspected article to the camera.

Further, for some embodiments, the objective lenses 211 may be infinitely conjugate (i.e., the objective lenses 211 may be located a focal length f away from the inspected article 130) so that the rays coming from the inspected article 130 are propagating parallel to each other after passing through the objective lenses 211, and do not diverge. This may allow a relatively long distance between an objective lens 211 and the tube lens 205 which, in conjunction with the objective lens 211, creates the image of the FOV onto the camera 206.

If reflected illumination is used (e.g., if the inspected article 130 is reflective), the image selection mirror 208 may also be used to illuminate the field of view (FOV) 224 for each objective 202 by directing light from the illumination source 209 to the FOV 224. By aligning the objective modules 202 in arcs 112, a constant distance between each objective module 202 and the illumination source 209 may be preserved. By preserving this constant distance, it is possible to image light from the illumination source onto an aperture of each objective module 202 (and fulfill the condition for Köhler illumination) which may provide uniform illumination of the objective FOV of each objective module 202.

For some embodiments, the illumination source 209 may be a pulsed source, such as a flash lamp, pulsed LED, or laser. For other embodiments, the illumination source 209 may be a continuous illumination source such as an arc lamp, filament lamp, continuous LED array or continuous laser. If the mirrors 208 scan continuously a light pulse can be used to freeze the image. The image may also be frozen in an effort to remove or reduce the influence of vibrations of the article or system. If continuous illumination is used, electronic or mechanical shutters for the camera 206 may also be used to freeze the image. If the mirrors 208 scan and settle at each FOV, the light integration by the camera can extend as long as the mirror is stable and as long as needed to integrate a suitable amount light.

For some embodiments, multiple images can be acquired for each FOV at different illumination and imaging configurations. The multiple images may be acquired simultaneously in the case of a continuous image selection mirror and short pulses of light, or consecutively in time in the case of scan and settle with long exposures. Various combinations of multiple illumination levels, imaging wavelengths, darkfield and brightfield, reflection and transmission levels, polarization states, focal planes, phase contrast, Diffractive Interference Contrast (DIC) and the like may be used to achieve greater contrast and enhance defect detection. These microscope illumination and imaging parameters may be varied to enhance the contrast of the defects relative to the background.

As illustrated in FIGS. 3A-3D, the image selection mirror 208 may be adjusted (e.g., rotated) to sequentially transfer images from each objective module 202 to the image plan 216 of the camera 206. FIGS. 3A-3D illustrate exemplary optical illumination and collection paths for two objective module $202_1$ and $202_2$.

Figure 3A:
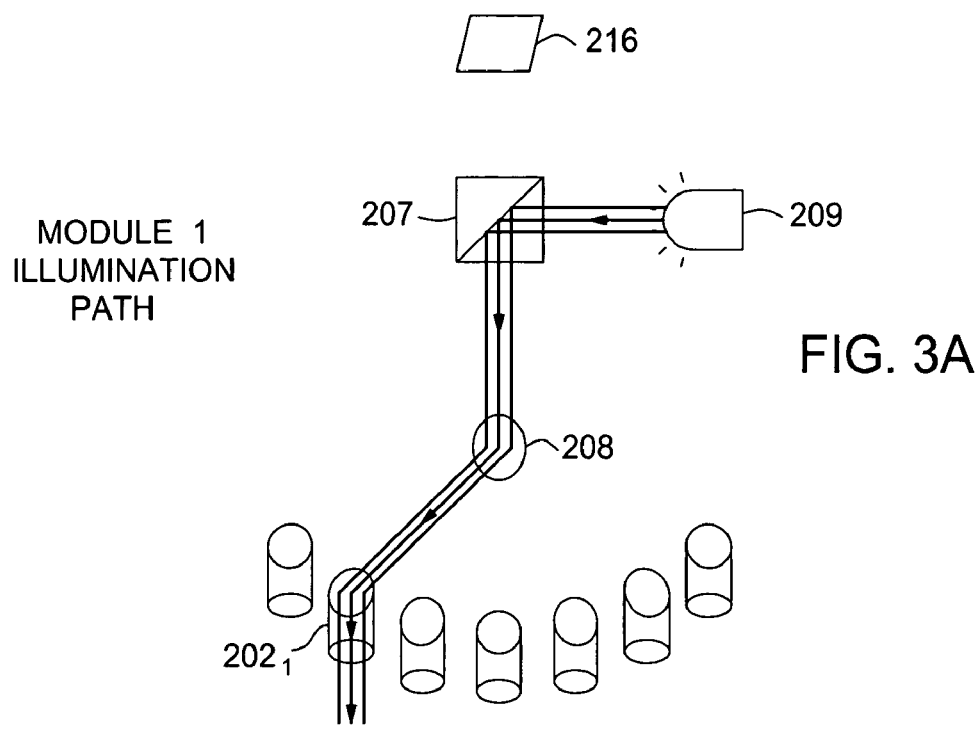
FIGS. 3A-3D illustrate exemplary optical illumination and capture paths in accordance with one embodiment of the present invention.
Figure 3B:
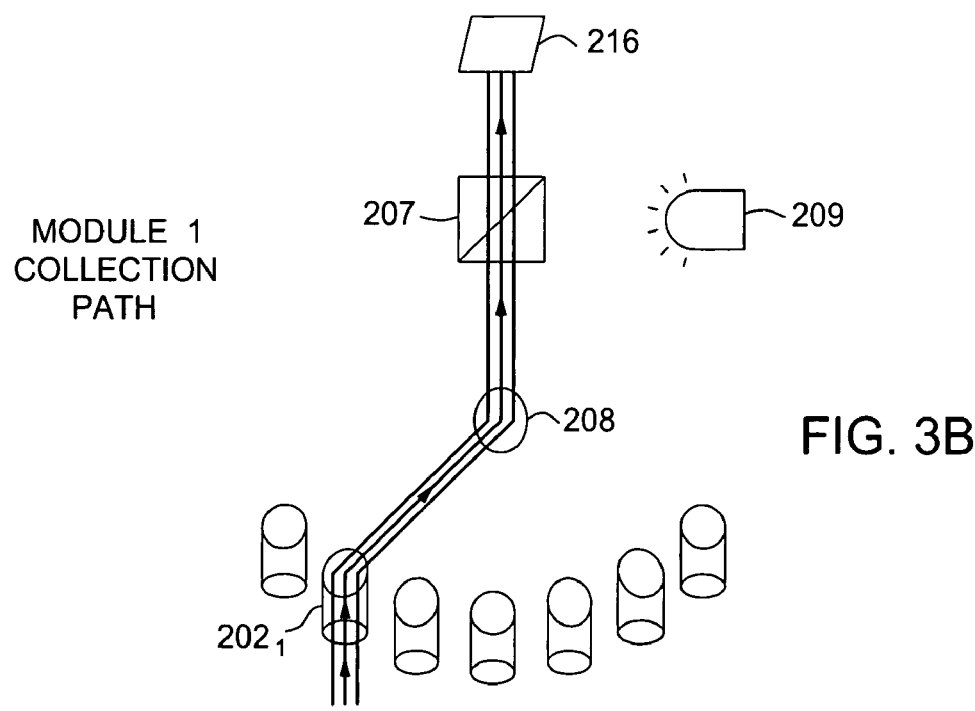
Figure 3C:
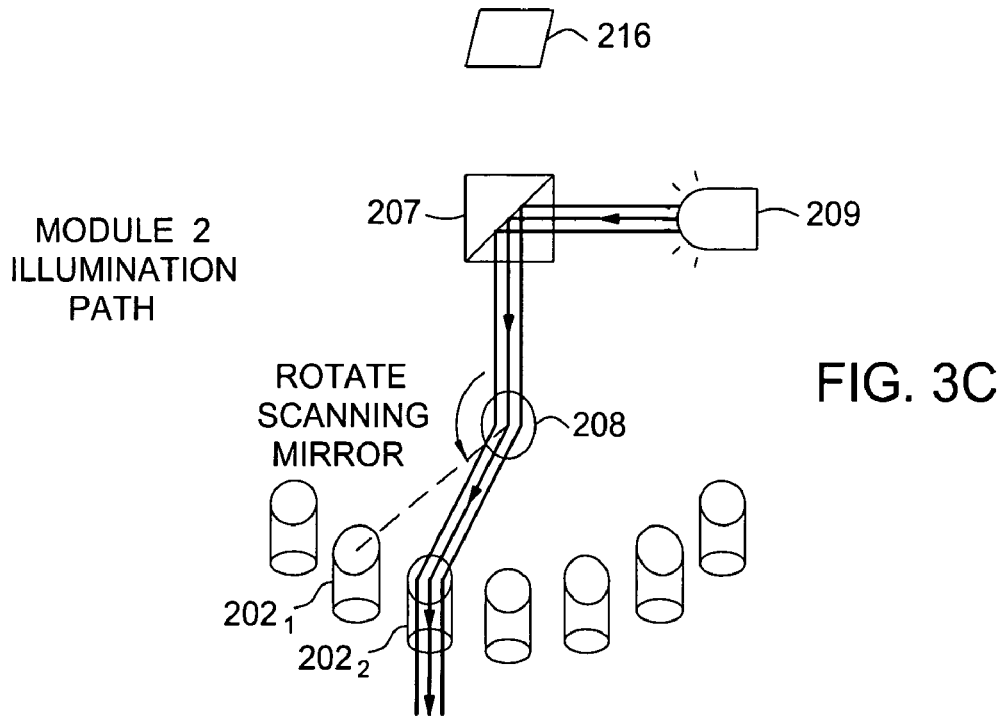
Figure 3D:
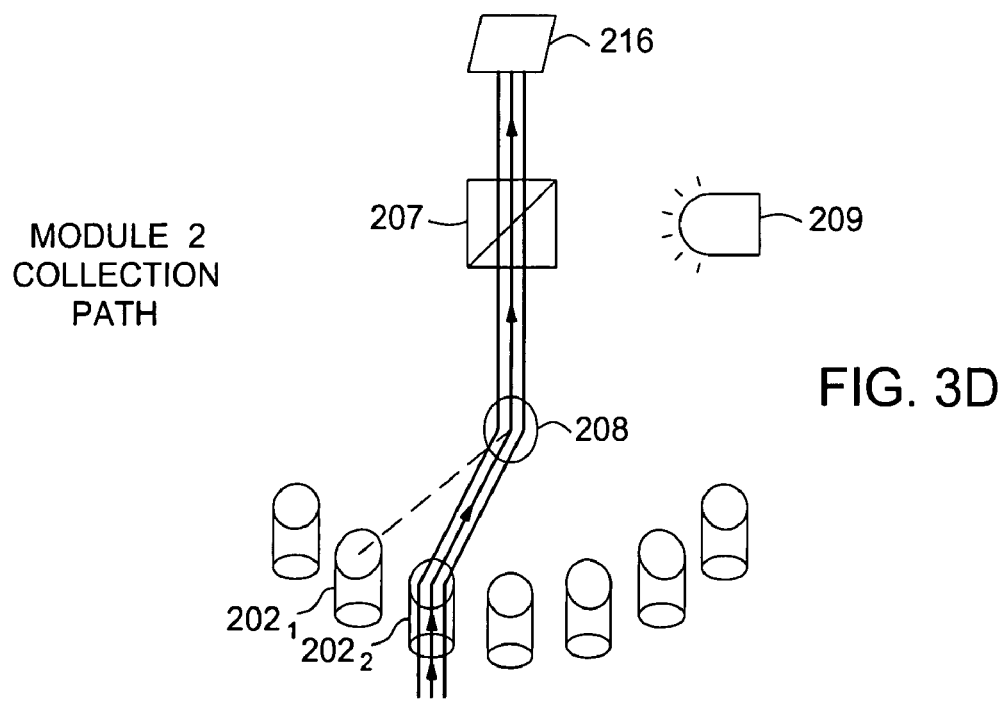

As illustrated in FIG. 3A, the image selection mirror 208 may be rotated in the direction of a first objective module $202_1$. In this position, the image selection mirror 208 may guide light from the illumination source 209 to the first objective module $202_1$, via the beam splitter 207, to illuminate a field of view 204 portion of the inspected article 130 below. As illustrated in FIG. 3B, light reflected from the illuminated FOV 224 is guided back through the objective $202_1$, via the beam splitter 207, to the image plan 216 of the camera 206. As illustrated in FIGS. 3C and 3D, the image selection mirror 208 may then be rotated in the direction of the second objective module $202_2$, in order to illuminate and capture the image of a different FOV 224 portion of the inspected article 130. Referring back to FIG. 2B, if the inspected article is specular reflective, an aperture stop 250 having an aperture 252 for each objective module 202 may be placed between the image selection mirror 208 and an arc 112 of objectives 202.

Figure 4:
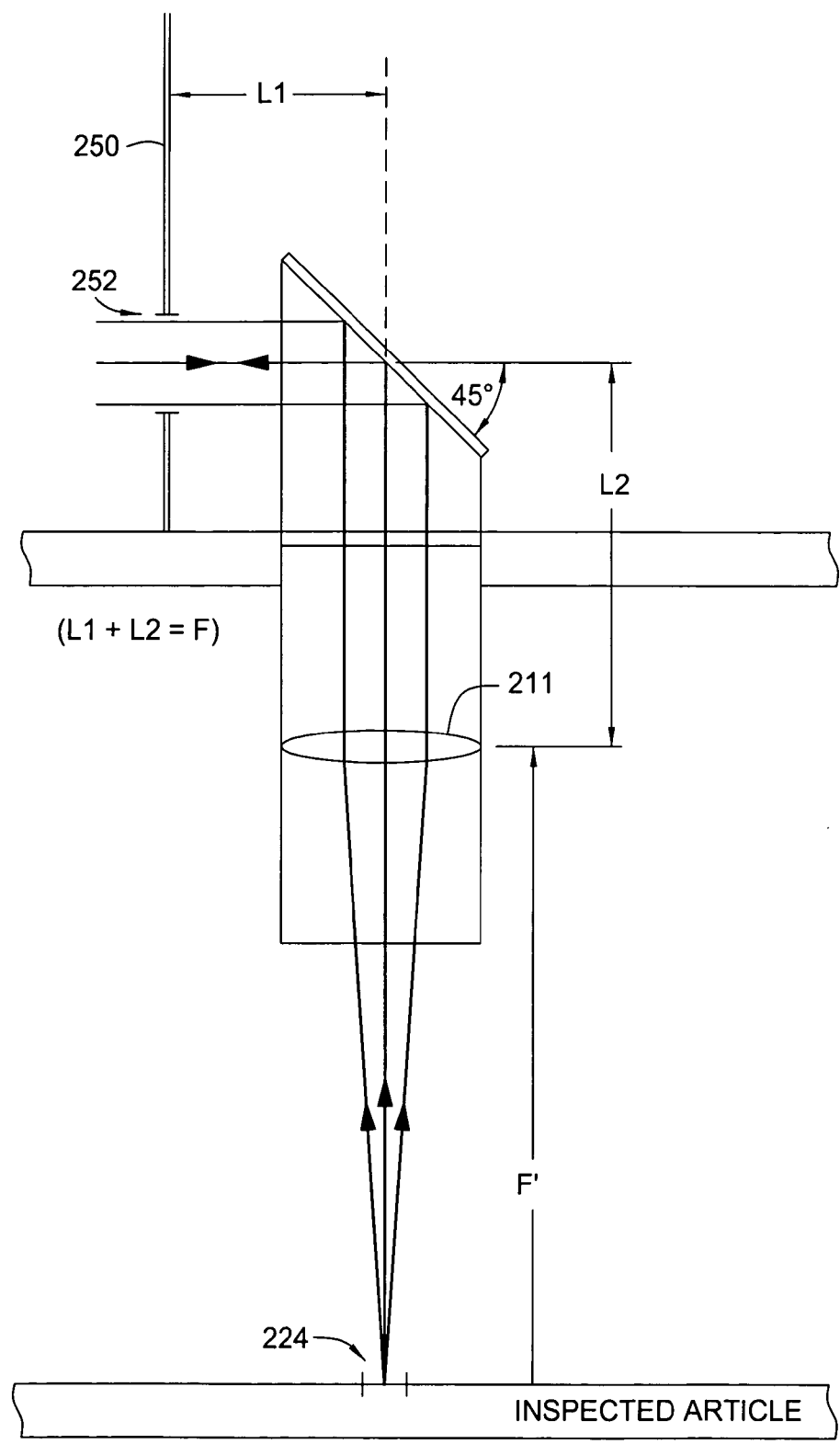
FIG. 4 illustrates an exemplary stop and aperture arrangement in accordance with one embodiment of the present invention.

As illustrated in FIG. 4, the aperture stop 250 may be placed a focal length (f) away from the principal plan of the objective lens 211 (e.g., the sum of the length L1 from the aperture stop 250 to the mirror 213 and the length L2 from the mirror 213 to the objective lens 211 may equal the focal length f) to direct the illumination rays in a telecentric way. This may ensure that the illuminating rays will be reflected back through the aperture stop 252 and into the camera 206, and will not be vingetted (blocked).

Those skilled in the art will recognize that many different arrangements of optical components (lenses, mirrors, optical relays, and prisms) may be used to divert the optical path from multiple objective modules 202 to a single camera 206. Various corrective mechanisms, such as speckle reduction modules, spatial filters, auto-focus modules, and the like, may also be utilized. For some embodiments, rather than using mirrors, prisms (not shown) may be used to divert the optical path from an objective module 202 to the camera 206. However, prism based systems may suffer from wavelength dispersion and optical distortion at the edges of the FOV. Therefore, prism based systems may include optical components to compensate for such dispersion and distortion.

Those skilled in the art will also recognize that the exact optical properties of the illustrated components will vary with different embodiments, for example, to meet the needs of a particular application (e.g., to achieve a desired resolution or throughput). As an example, however, for some embodiments, the objective lenses 211 may have a rectangular field of view between 3 mm×3 mm to 8 mm×8 mm, an NA in the range of 0.03-0.06, a focal length in the range of 70-125 mm, and an approximate magnification in the range of 1-2. The camera 206 may have any number of pixels, and, for some embodiments, may be in a common range between 600×400 to 2000×2000 pixels, with a pixel size in the range of 7-15 micron. The illuminating source 207 may generate broadband light in the visible wavelength range and may be controlled to ensure the detected light (reflected by or transmitted through the inspected article 130) saturates the camera 206, which may be any suitable type of image sensing device, such as a CCD camera or CMOS sensor. Those skilled in the art will recognize that multiple wavelengths may also be utilized. Utilizing components with such properties, an image scanning module 110 may have an image acquisition time (the time required to obtain an image from each objective) in the range of 5-50 us. Those skilled in the art will recognize that greater resolution may be achieved by varying any number of the parameters described above, for example, by increasing the NA of the lenses, decreasing the field of view, and/or increasing the pixel size of the camera. Further, for some embodiments, in an effort to improve throughput, multiple cameras may be utilized per image scanning module (e.g., at least one camera for each arc).

Exemplary Objective Layout

In order to ensure full coverage of the inspected article 130, the total number of objective modules 202 may, at a minimum, be the total width of the article 130 to be inspected ($W_I$) divided by the individual FOV 224 of each objective module 202 minus an overlap area between FOVs (to allow for some tolerance in objective placement and/or movement of the article 130). As shown in FIG. 2B, the objective modules 202 in each image scanning module 110 may be arranged in arcs 112 that are shifted relative to each other in a direction perpendicular to the direction of travel of the inspected article 130, by one FOV width minus the overlap area to ensure there are no un-covered areas between the FOVs. The actual number of arcs 112 may be chosen based on various considerations, such as the actual spacing of objective modules 202 in each arc 112, the number of times the image selection mirror 208 is able to stop in the time given from the throughput requirements of the system (each stop to address an objective module involves acceleration and deceleration), or other considerations, As shown in FIG. 2A, a number of image scanning modules 110 may be arranged to cover an entire width of the article 130 to be inspected, with pairs of image scanning modules 110 covering corresponding regions 132.

Figure 5A:
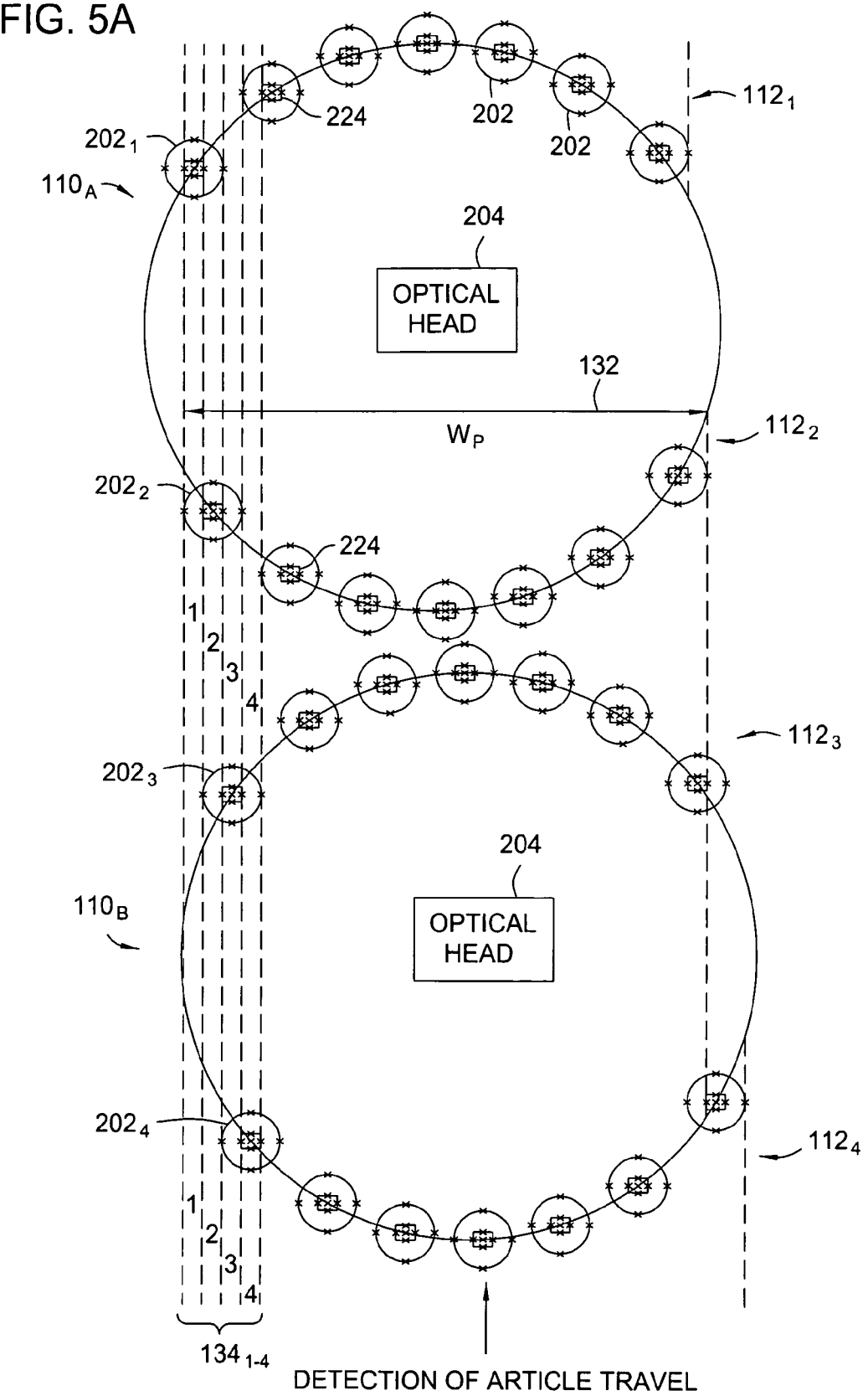
FIGS. 5A-5E illustrate exemplary objective layouts in accordance with embodiments of the present invention.

FIG. 5A illustrates a top view of an exemplary arrangement of such image scanning modules 110 and corresponding objective modules 202 arranged in arcs 112, suitable to inspect a region 132 (having a width $W_P$) of an article 130. As described above, in an effort to cover the entire width of the inspected article 130 with the collective coverage of the FOVs 224 (with at least some partial overlap) of the individual objective modules 202, multiple image scanning modules $110_A$ and $110_B$ may be placed in series along the direction of travel of the article 130 and offset (e.g., horizontally) relative to each other.

As illustrated, the inspected region 132 may be conceptually divided into adjacent columns 134, with any four adjacent columns (e.g., $134_1$-$134_4$) being covered by a FOV 224 of an objective module 202 in a different arc 112. For example, FOVs of objective modules $202_1$ and $202_2$ in arcs $112_1$ and $112_2$, respectively, of the image scanning module $110_A$ may cover first and second columns $134_1$ and $134_2$. Similarly, FOVs of objective modules $202_3$ and $202_4$ in arcs $112_3$ and $112_4$, respectively, of the image scanning module $110_B$ may cover third and fourth columns $134_3$ and $134_4$. The remaining objectives 202 in each arc 112 may be arranged in a similar manner to ensure each column of the entire width $W_P$ of region 132 is covered, with at least some overlap.

As previously described and shown in FIG. 2A, any suitable number of additional pairs of image scanning modules 110 may be arranged horizontally (e.g., perpendicular to the article direction of travel) to cover different regions 132 of the entire width of the inspected article 130. Those skilled in the art will recognize that the particular arrangement shown in FIG. 5A is illustrative only and that image scanning modules 110 with various other arrangements of objective modules 202 may also be used to inspect an entire width of an article 130.

Figure 5B:
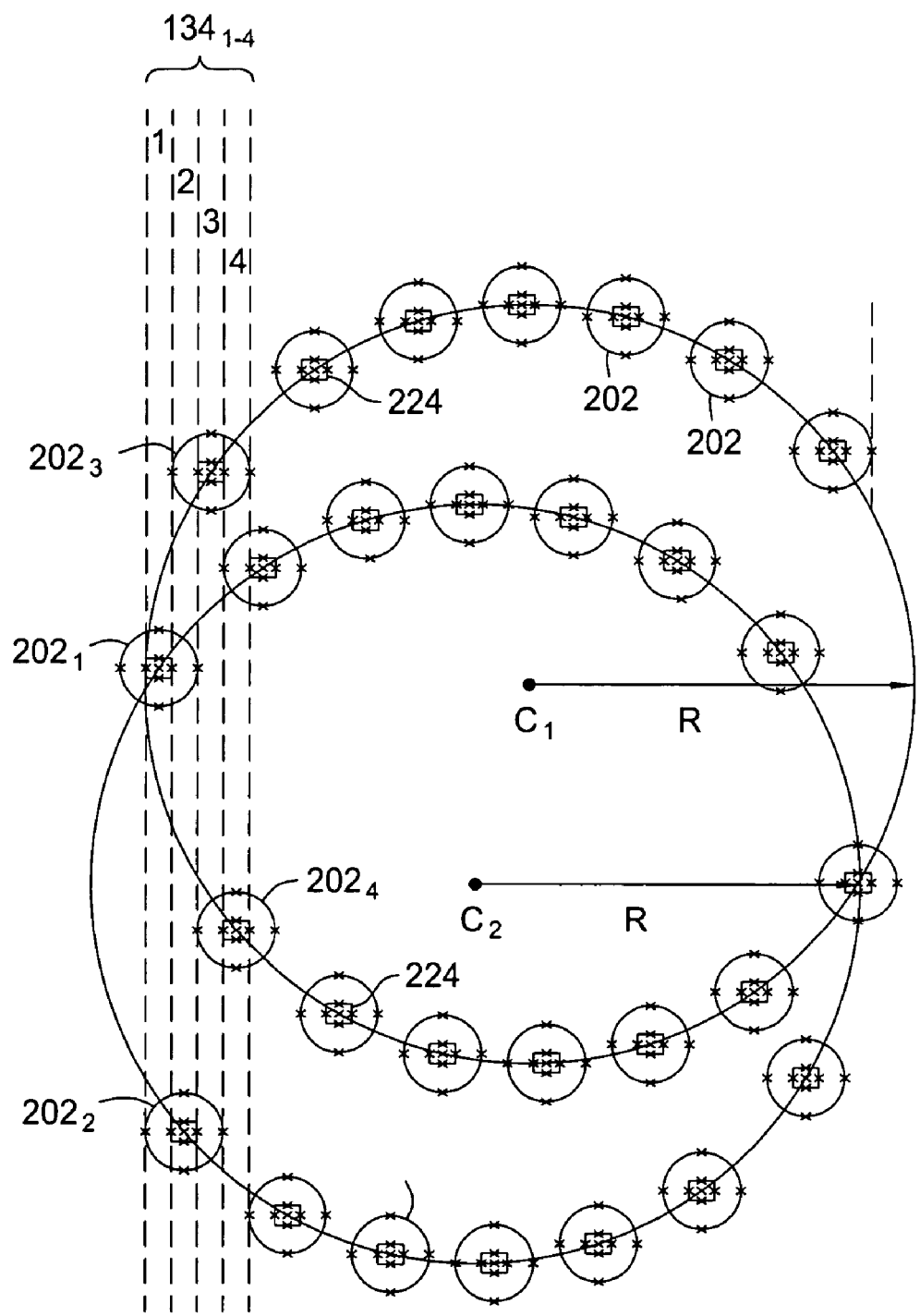

FIG. 5B illustrates one example of an alternative arrangement of objective modules 202, in which multiple arcs 112 of objective modules 202 are arranged as partially overlapping circles having a common radius r, with centers C1 and C2 offset relative to each other. As with the arrangement shown in FIG. 5A, adjacent columns $134_1$-$134_4$ may be covered by objective modules 202 in different arcs $112_1$-$112_4$. Each circle of objectives may have an optical head (not shown) with a camera and an image selection mirror that rotates around the respective center to capture an image from each objective 202. In this arrangement, some type of provisions may be made to ensure that one optical head does not block the light rays of another optical head. Such provisions may include, for example, providing apertures in the structure of one optical head to let rays from another optical head pass to its objectives.

Figure 5C:
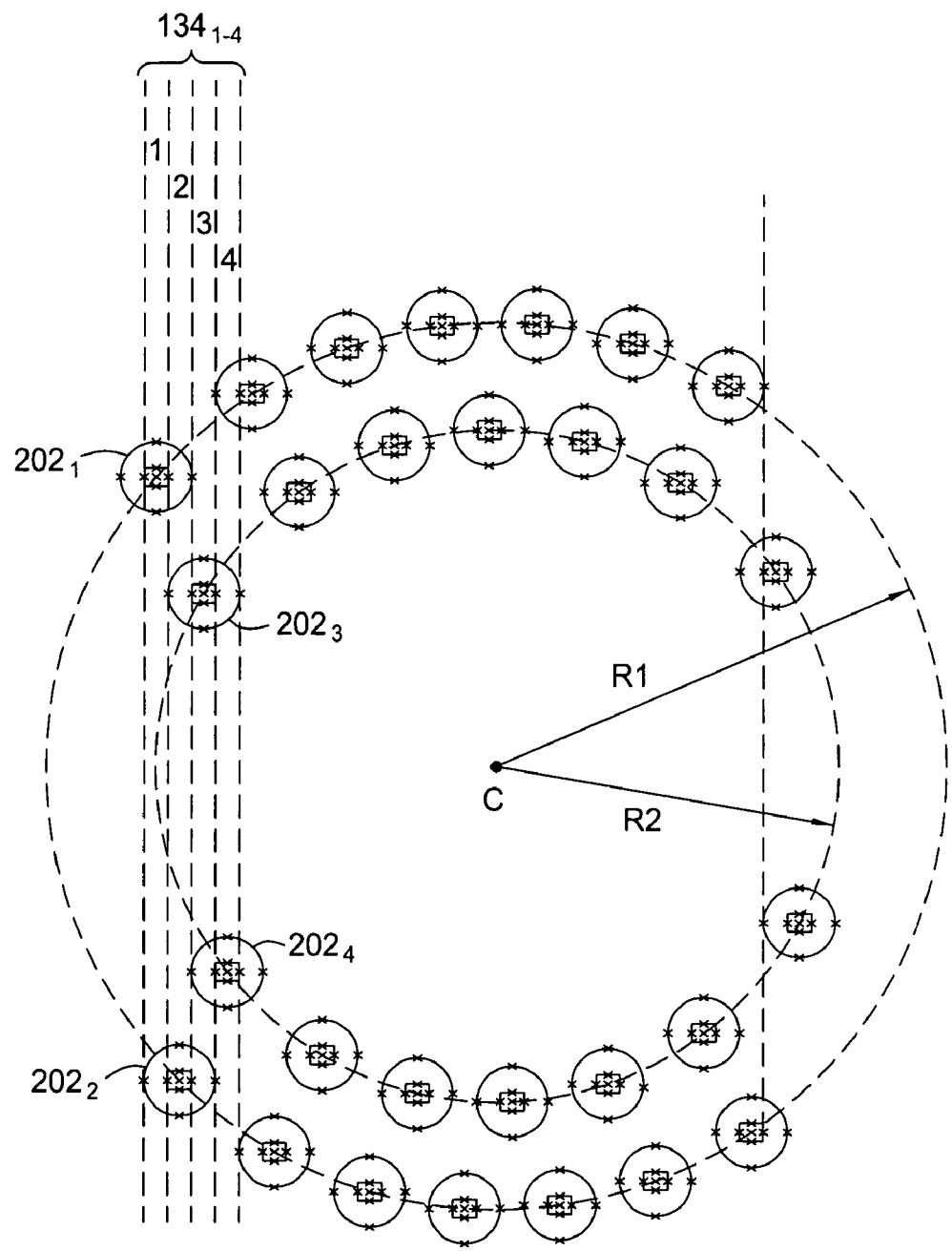

Another example of an alternative arrangement of objective modules 202, illustrated in FIG. 5C, has multiple arcs 112 of objective modules 202 arranged as concentric circles (having a common center C) with different radii r1 and r2. As with the arrangements shown in FIGS. 5A and 5B, adjacent columns $134_1$-$134_4$ may be covered by objective modules 202 in different arcs $112_1$-$112_4$. Illustratively, objective modules $202_1$ and $202_2$ in arcs 112 forming the outer concentric circle cover regions $132_1$ and $132_2$ while objective modules $202_3$ and $202_4$ in arcs 112 forming the inner concentric circle cover regions $132_3$ and $132_4$. As with the arrangement described above, some type of provisions may be made to ensure that one optical head does not block the light rays of another optical heads. Such provisions may include folding the optical path of one optical head into a different plane, utilizing image selection mirror mechanisms with hollow (or otherwise transparent) shafts, and the like.

Figure 5D:
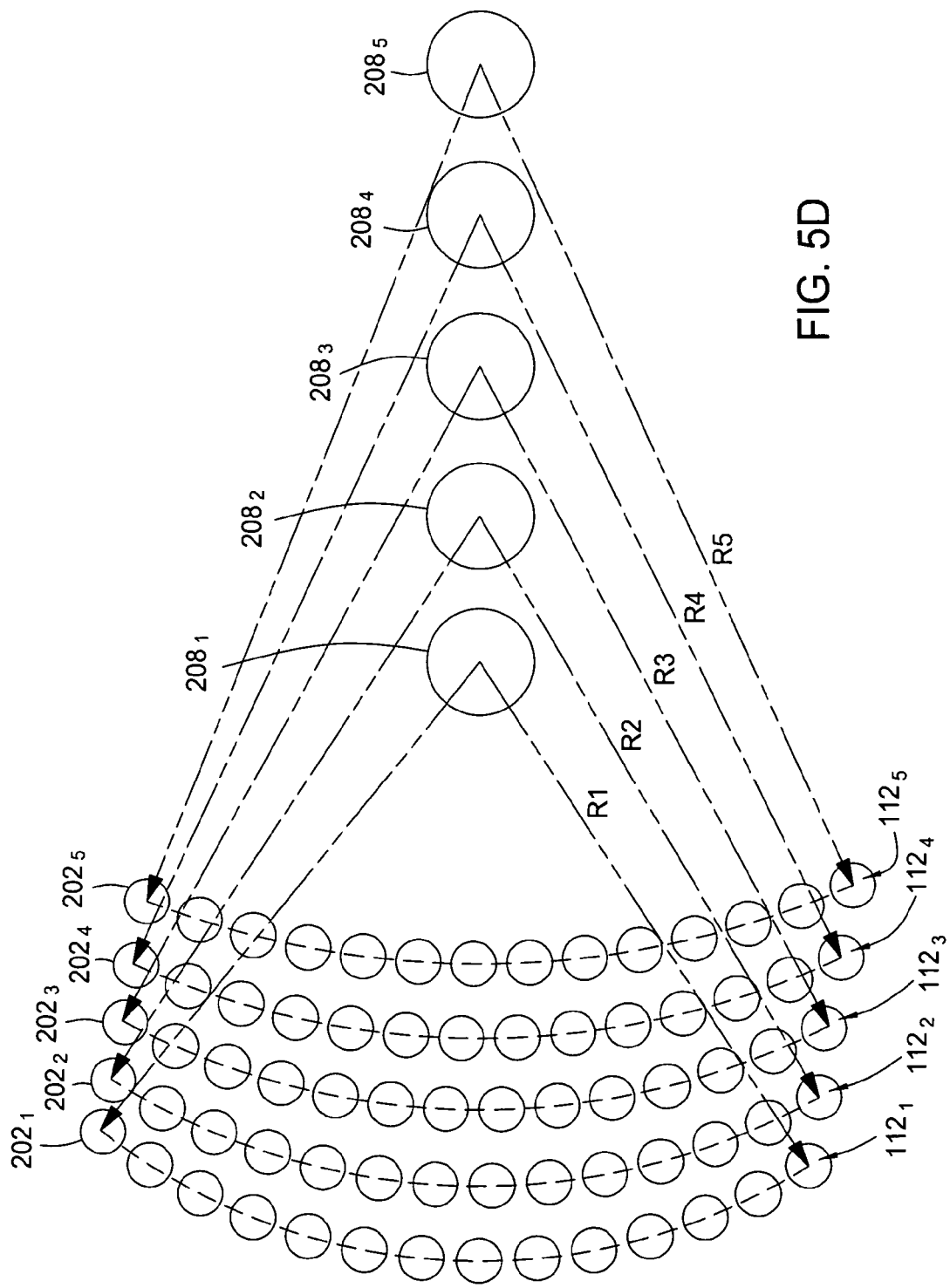
Figure 5E:
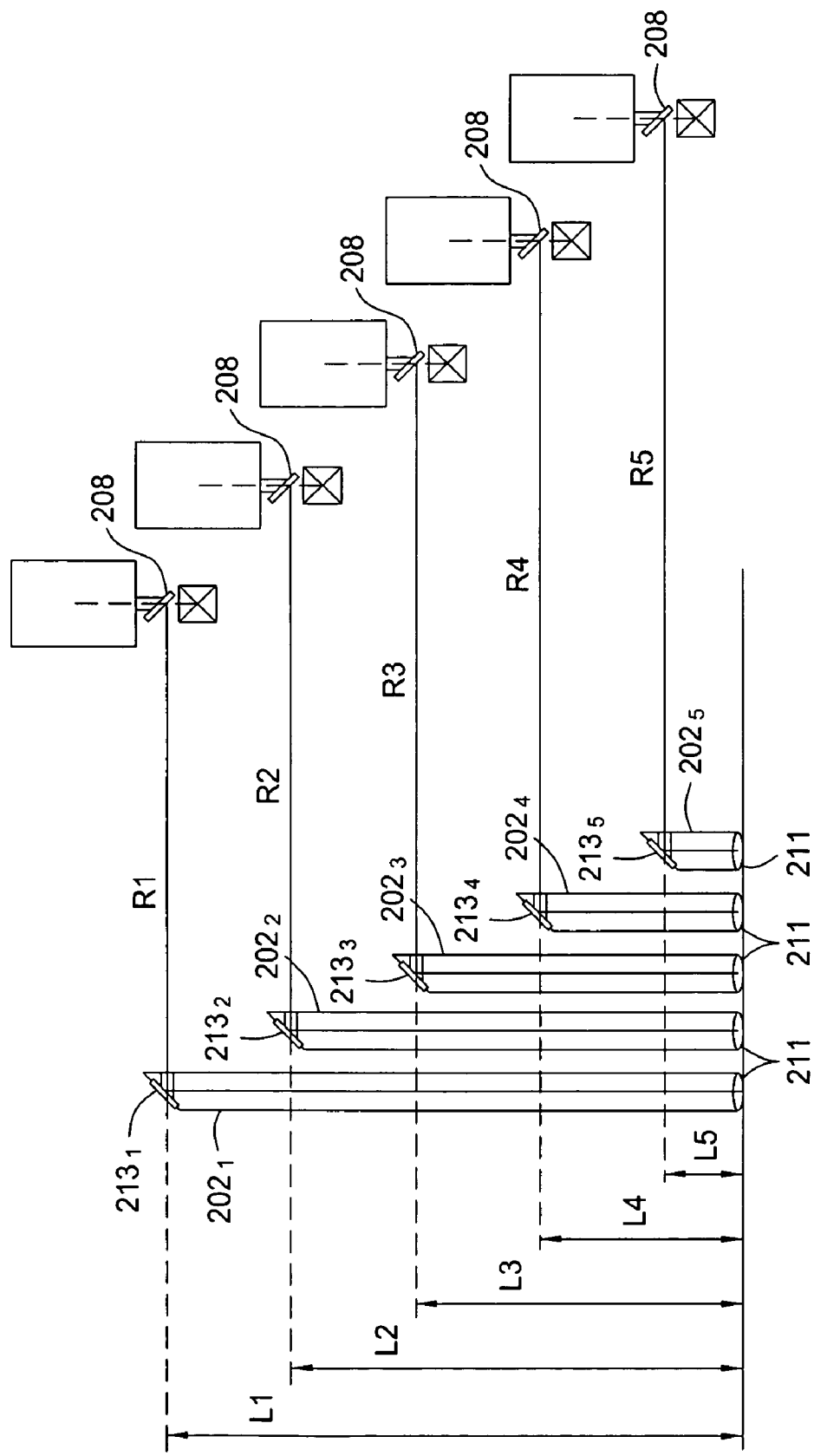

For some embodiments, an objective arrangement may include partially overlapping arcs of objective modules, with the radius of each arc and distance between the objective mirror and front lens for the corresponding objective modules varied to maintain a consistent optical path length. Maintaining a consistent optical path length may allow a common optical design (utilizing common optical components) to be used in the multiple arcs. FIG. 5D illustrates a top view of such an arrangement, having five overlapping arcs $112_{1\text{-}5}$ of objective modules $202_{1\text{-}5}$ having different radii r1-r5, respectively. As illustrated in the side view shown in FIG. 5E, the distances $I_{1\text{-}5}$ from the objective mirror 213 to front lens 211 of the objective modules $202_{1\text{-}5}$ in the arcs $112_{1\text{-}5}$ may be varied in an effort to maintain a consistent optical path from the image selection mirror 208 to the objective lens 211 for each arc (e.g., I1+r1=I2+r2=I3+r3=I4+r4=I5+r5).

Those skilled in the art will also recognize that, while arranging objectives 202 in arcs 112 may facilitate uniform illumination by preserving a constant distance between the illuminating source and objective lens, objective modules may be arranged in other patterns, such as linear rows of objective modules 202 offset from each other to provide at least partially overlapping coverage of an inspected portion of an article.

In the objective arrangements described herein, the distance between the objective lenses 211 and the camera 206 and illumination source 209 may be relatively large when compared to conventional microscopes used for similar purposes. This distance may grow with the number of objectives scanned per camera. As previously described, to enable such long distances, the objective lenses 211 may be infinitely conjugate such that the rays from a single field points are collimated at the exit of the objective lens, or another lens may be put along the optical pass. In some cases, the practical limitations on this distance and hence on the number of objectives and the length of the optical path may come from the field span of the rays (the angular divergence of beams from the extreme field points), which may be limited by the practical size of the image selection mirror.

Figure 6:
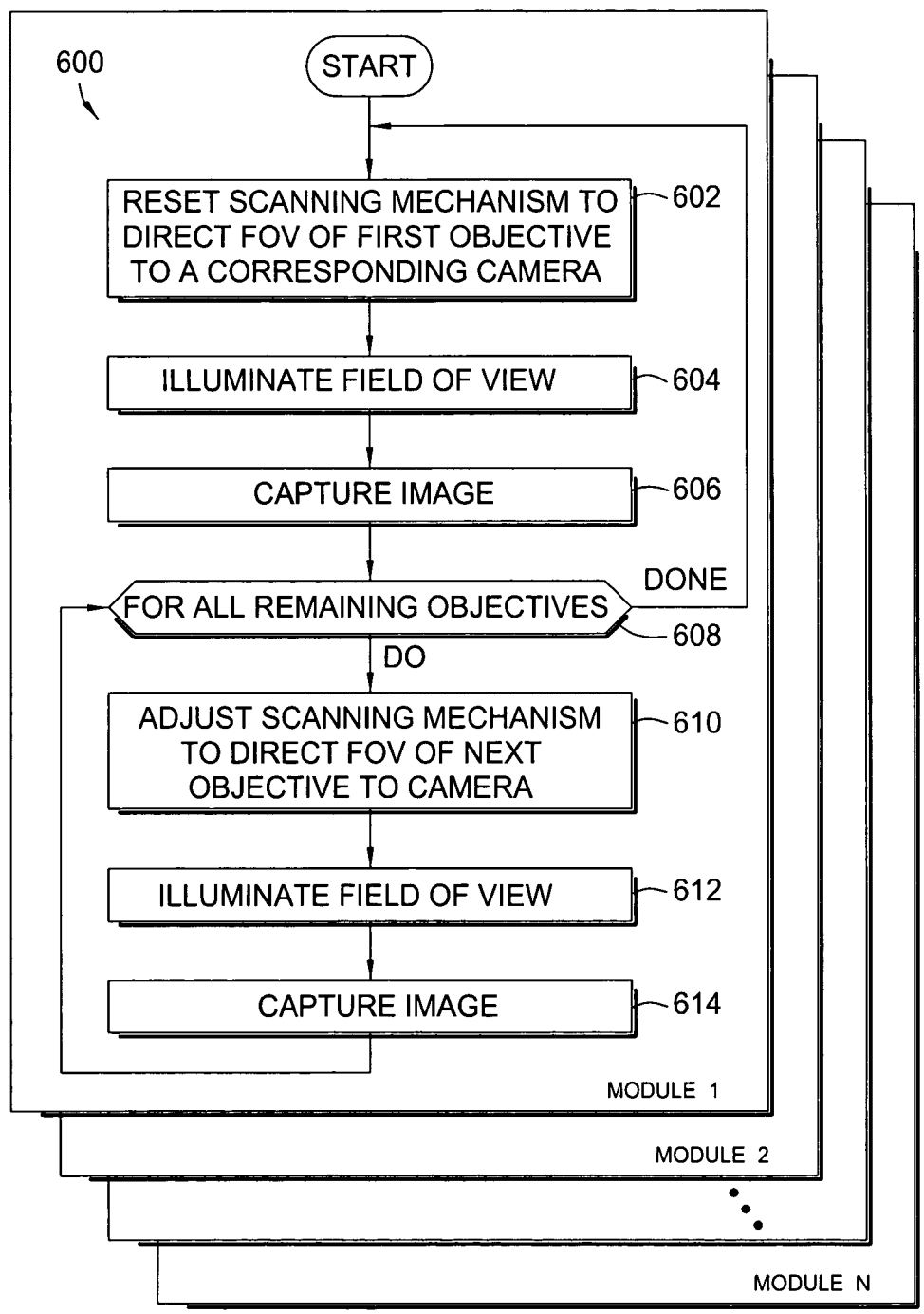
FIG. 6 illustrates exemplary operations for optically inspecting an article in accordance with one embodiment of the present invention.

FIG. 6 illustrates exemplary operations 600 that may be performed to sequentially scan each objective module 202 (e.g., in one or more arcs) in an image scanning module 110. As previously described, the scanning mechanism 110 may be arranged so that objective modules 202 in different rows may be scanned simultaneously. Thus, similar operations 600 may be performed for each module concurrently (in parallel).

The operations 600 begin, at step 602, by resetting the scanning mechanism for an image scanning module 110 to direct a field of view of a first objective to a corresponding camera. For example, referring to FIG. 2B, the image selection mirror 208 may be rotated to steer its optical axis to the left-most objective module 202 to illuminate a corresponding FOV on the inspected article and transfer an image therefrom. At step 604, the field of view of the first objective is illuminated and, at step 606, the image is captured with the camera.

At step 608, a loop of operations 610-614, to be performed for each of the remaining objectives in the module, is entered to capture image portions therefrom. At step 610, the scanning mechanism is adjusted to direct the field of view of the next objective to the camera. At step 612, the field of view is illuminated and, at step 614, the image is captured. Once the operations 610-614 have been performed for each of the remaining objectives, the operations may return, to step 602, to again reset the scanning mechanism to direct the field of view of the first objective to the camera, in preparation of scanning the row again, to capture images of the portion of the inspected article 130 that has now traveled between the objectives. In an effort to ensure the entire portion of the article to be inspected is scanned, this cycle of operations may be performed synchronized with the article translation mechanism. In other words, the image selection mirror and translation mechanism may be controlled such that these operations may be performed in the same amount of time it takes for the inspected article is to travel one length of the FOV (the dimension parallel to the media travel direction) minus some pre-determined overlap between the FOV. The amount of this overlap may be determined by the tolerance in the travel of the inspected article.

For some embodiments, in order to detect defects, images from different rows may be pieced or "stitched" together to form a larger, more complete image of the article which is then processed. For other embodiments, however, the individual FOV images obtained from each objective may be sufficient for defect detection. This may be the case when the scale of such a defect allows the entire defect to be contained within a single FOV and the objectives are arranged to ensure the entire width of the inspected article 130 is covered with at least some partial overlap.

In any case, various image processing techniques may be utilized to detect defects based on captured images. For example, captured image portions may be compared against known good images (e.g., stored in a database), against images captured from a known good (or "golden") article, or "statistical" images with/without defects of interest, or by comparison of one pattern in the article to an identically designed pattern (e.g., a "die to die" or "cell to cell" comparison).

CONCLUSION

Embodiments of the present invention provide high throughput optical inspection with moderate cost by reducing the number of cameras and illumination sources when compared to conventional multi-microscope systems utilizing a camera and illumination source for each microscope. Further, by freezing individual field of view images, the translation system (e.g., conveyer) motion accuracy requirements may be greatly reduced when compared to scanning systems (e.g., "flying spot laser scanning systems"). Inaccuracies in the coverage of the article by the multiple objectives may also be compensated for by at least partially overlapping fields of view.

While the foregoing is directed to embodiments of the present invention, other and further embodiments of the invention may be devised without departing from the basic scope thereof, and the scope thereof is determined by the claims that follow.

We claim:

1. An automated optical inspection system, comprising:
at least one camera; and
at least one image scanning module comprising a plurality of objective modules arranged to have fields of view covering a portion of an article during inspection and an image selection mirror mechanism movable to sequentially select and transfer images from the fields of view from the objective modules to the at least one camera.

2. The system of claim 1, wherein the objective modules comprise an objective lens and a mirror for transferring images from the objective lens to the image selection mirror mechanism.

3. The system of claim 2, wherein:
the plurality of objective modules in the image scanning module are arranged in a linear row.

4. The system of claim 2 wherein the plurality of objective modules in the image scanning module are arranged in an arc.

5. The system of claim 4, wherein the objective modules are arranged in at least one arc centered around the image selection mirror mechanism.

6. The system of claim 5, wherein:
the system further comprises at least one illumination source; and
a field of view portion of the article is illuminated by directing light from the illumination source to the field of view portion through an objective module via the image selection mirror mechanism.

7. The system of claim 1, further comprising an article translation mechanism to move the article relative to the image scanning module.

8. The system of claim 1, wherein the image scanning module is movable relative to the article during inspection.

9. The system of claim 1, further comprising a mechanism to sense relative motion between the article and the image scanning module to determine a position of the article relative to the image scanning module.

10. The system of claim 1, further comprising at least one illumination source.

11. The system of claim 10, wherein the illumination source comprises a pulsed light emitting diode (LED).

12. The system of claim 10, wherein the illumination source comprises a flash lamp.

13. The system of claim 10, wherein the system comprises at least one illumination source for each camera.

14. An automated optical inspection system for inspecting an article, comprising:
at least one camera; and
at least one image scanning module comprising a plurality of objective modules with fields of view covering a portion of the article during inspection and an image selection mirror mechanism movable to sequentially select and transfer images from the fields of view from the objective modules to the camera, wherein the objective modules are arranged in at least one arc centered around the image selection mirror mechanism.

15. The system of claim 14, wherein:
the objective modules are arranged in at least two arcs centered around the image selection mirror mechanism; and
fields of view of the objective modules of a first one of the arcs at least partially overlap with fields of view of the objective modules of a second one of the arcs.

16. The system of claim 15, comprising:
a plurality of cameras; and
a corresponding plurality of image scanning modules, wherein the collective objective modules of the plurality of image scanning modules are arranged such that an entire width of the article under inspection is covered by the combined fields of view of the collective objective modules.

17. The system of claim 14, wherein the at least one image scanning module further comprises a stop mechanism positioned between the image selection mirror mechanism and the plurality of objective modules, wherein the stop mechanism has a plurality of apertures corresponding to the plurality of objective modules.

18. The system of claim 17, wherein:
the stop mechanism is located approximately a focal length, in the optical path, away from objective lenses of the objective modules.

19. The system of claim 14, wherein the objective modules comprise an objective lens and a folding mirror for transferring images from the objective lens to the image selection mirror mechanism.

20. The system of claim 19, wherein:
the objective module folding mirror is positioned at approximately forty-five degrees to an optical path beyond the objective lens;
the image selection mirror mechanism has a plan at approximately forty-five degrees to its rotation axis to direct light rays transmitted from the objective module mirror in a direction substantially parallel to its rotation axis.

21. The system of claim 14, wherein the objective modules are arranged to have at least partially overlapping fields of view.

22. A method for inspecting an article, comprising:
bringing at least a portion of the article in fields of view of at least one of a plurality of objective modules;
adjusting an image selection mirror mechanism to sequentially direct images of the field of view from the objective modules to at least one camera shared by the objective modules;
capturing the images with the shared camera; and
processing the captured images to detect defects in the article.

23. The method of claim 22, wherein bringing at least a portion of the article in fields of view of at least one of a plurality of objective modules comprises moving the article via a translating mechanism.

24. The method of claim 22, wherein adjusting the image selection mirror mechanism comprises moving the mirror mechanism to direct an image from a field of view of an objective module to the shared camera.

25. The method of claim 24, wherein moving the image selection mirror mechanism comprises rotating the image selection mirror mechanism.

26. The method of claim 24, further comprising illuminating the fields of view of the objective modules with light provided from an illumination source via the image selection mirror mechanism.

27. The method of claim 26, wherein the objective modules are arranged in at least one arc centered around the image selection mirror mechanism.

28. The method of claim 27, wherein illuminating the fields of view of the objective modules with light provided from an illumination source via the image selection mirror mechanism comprises directing light from the image selection mirror mechanism to the objective modules through apertures in a stop mechanism.

* * * * *